(12) United States Patent
Howlett et al.

(10) Patent No.: US 6,358,990 B1
(45) Date of Patent: Mar. 19, 2002

(54) METHOD FOR TREATING ALZHEIMER'S DISEASE

(75) Inventors: David Robert Howlett, Bishop's Stortford; Davina Elizabeth Mitchell, Shelly Ongar, both of (GB)

(73) Assignees: Boehringer Mannheim Pharmaceuticals Corp.; SmithKline Beckman Corp. Limited Partnership No. 1, both of Gaithersburg, MD (US)

( * ) Notice: Subject to any disclaimer, the term of this patent is extended or adjusted under 35 U.S.C. 154(b) by 0 days.

(21) Appl. No.: 09/529,526
(22) PCT Filed: Oct. 15, 1998
(86) PCT No.: PCT/US98/21789
 § 371 Date: Apr. 13, 2000
 § 102(e) Date: Apr. 13, 2000
(87) PCT Pub. No.: WO99/18794
 PCT Pub. Date: Apr. 22, 1999

Related U.S. Application Data
(60) Provisional application No. 60/062,366, filed on Oct. 15, 1997.

(51) Int. Cl.$^7$ ............................................... A61K 31/40
(52) U.S. Cl. ..................................................... 514/411
(58) Field of Search ........................................ 514/411

(56) References Cited

U.S. PATENT DOCUMENTS 4,983,608 A    1/1991  Effland et al. ............... 514/256

OTHER PUBLICATIONS

Hibino, et al., Database HCAPLUS on STN, No. 1993:495333.

*Primary Examiner*—Theodore J. Criares
(74) *Attorney, Agent, or Firm*—Mary E. McCarthy; Stephen Venetianer; Charles M Kinzig

(57) ABSTRACT

A method of treating amyloid diseases by administering a compound of Formula I:

(I)

wherein:
 $R_7$–$R_{13}$ are independently —H or —OH; and
 A is H, —OH, or a moiety of Formula II:

(II)

wherein:
 $R_1$ is hydrogen, lower alkanoyl of up to 6 carbon atoms or aroyl selected from benzoyl and naphthoyl;
 $R_2$ is hydrogen, lower alkyl of up to 6 carbon atoms or arylalkyl selected from benzyl, phenylethyl and phenylpropyl;
 $R_3$ is hydrogen or lower alkyl of up to 6 carbon atoms;
 $R_4$ is hydrogen or lower alkyl of up to 6 carbon atoms, or when X is oxygen, $R_4$ together with $R_5$ can represent —$CH_2$—O—;
 X is a valency bond, —$CH_2$, oxygen or sulfur;
 Ar is selected from phenyl, naphthyl, indanyl and tetrahydronaphthyl;
 $R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or
 $R_5$ and $R_6$ together represent methylenedioxy; or a pharmaceutically acceptable salt thereof, for treating amyloid diseases, and, thus, having utility in the treatment of Alzheimer's disease.

11 Claims, No Drawings

METHOD FOR TREATING ALZHEIMER'S DISEASE

This application claims the benefit of U.S. Provisional Application No. 60/062,366 filed Oct. 15, 1997.

FIELD OF THE INVENTION

The present invention relates to a novel method for treating amyloid diseases, in particular Alzheimer's disease, using carbazole compounds of Formula I, preferably carvedilol or hydroxylated derivatives of carvedilol.

BACKGROUND OF THE INVENTION

Amyloid diseases are characterized by the presence of extracellular ordered, but non-crystalline, protein aggregates comprised of cross-β-fibril/antiparallel β-sheets formed through incorrect protein folding. Amyloid is usually pathogenic. The most common clinical amyloidoses are Alzheimer's disease, chronic inflammation, multiple myelomas, Type II diabetes and Creutzfeldt-Jacob disease. Amyloid diseases may cause cardiac problems in old age familial amyloid polyneuropathy, and may also create the need for long-term dialysis. A general amyloidosis inhibitor could be beneficial in treating amyloid diseases, since systemic amyloid formation is reversible, and existing amyloid deposits may be resorbed, once the rate of deposition is slowed or halted.

Alzheimer's disease (AD) is the most common cause of dementia in old age, and afflicts 5–10% of all individuals over the age of 65 years. Characteristic changes in the brain include senile plaques, neurofibrillary tangles, and the degeneration and loss of neurons. Senile plaques are located extracellularly and contain deposits of fibrillar β-amyloid, the most important component of which is the βA4 peptide. Aggregated forms of βA4 are toxic to cultured neurons in vitro [L. Iverson et al., *Biochem. J.*, 311, 1–16 (1995)], and the formation and aggregation of βA4 in the brain is an essential early mediator of the pathology of AD.

Surprisingly, it has been found that carvedilol and related Formula I compounds are useful for treating amyloid diseases. In particular these compounds are useful in inhibiting the formation of the neurotoxic βA4 oligomeric aggregate, and, thus, they would be useful in the treatment of Alzheimer's disease.

SUMMARY OF THE INVENTION

The present invention provides a new method of using compounds which are dual non-selective β-adrenoceptor and $\alpha_1$-adrenoceptor antagonists, in particular the carbazolyl-(4)-oxypropanolamine compounds of Formula I, preferably carvedilol, in the treatment of amyloid diseases.

The present invention also provides a new method of treatment using compounds which are dual non-selective β-adrenoceptor and $\alpha_1$-adrenoceptor antagonists, in particular the carbazolyl-(4)-oxypropanolamine compounds of Formula I, preferably carvedilol, for inhibiting the formation of the neurotoxic βA4 oligomeric aggregate, in mammals, particularly in humans. In particular, the present invention provides a method using said compounds for treating Alzheimer's disease.

This invention further provides a method for treating Alzheimer's disease which comprises administering step-wise or in physical combination a compound of Formula I and a cognition enhancer, such as Memric.

DETAILED DESCRIPTION OF THE INVENTION

The present invention provides a new method of using compounds which are dual non-selective β-adrenoceptor and $\alpha_1$-adrenoceptor antagonists, in particular the carbazolyl-(4)-oxypropanolamine compounds of Formula I, preferably carvedilol, in the treatment of amyloid diseases. In particular, the present invention provides a new method for inhibiting the formation of the neurotoxic βA4 oligomeric aggregate using compounds which are dual non-selective β-adrenoceptor and $\alpha_1$-adrenoceptor antagonists. Preferably, this invention provides a new method for inhibiting the formation of the neurotoxic βA4 oligomeric aggregate, in particular in the treatment of Alzheimer's disease, using compounds of Formula I:

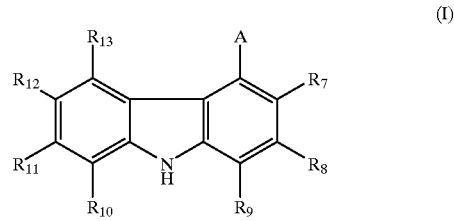

(I)

wherein:

$R_7$–$R_{13}$ are independently —H or —OH; and

A is H, —OH, or a moiety of Formula II:

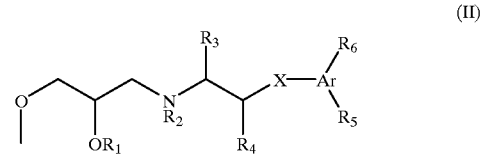

(II)

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —CH$_2$—O—;

X is a valency bond, —CH$_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

or a pharmaceutically acceptable salt thereof.

More preferably, the present invention provides a new method for inhibiting the formation of the neurotoxic βA4 oligomeric aggregate using compounds of Formula III:

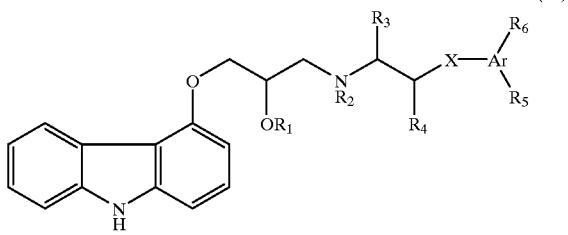

(III)

wherein:
- $R_1$ is hydrogen, lower alkanoyl of up to 6 carbon atoms or aroyl selected from benzoyl and naphthoyl;
- $R_2$ is hydrogen, lower alkyl of up to 6 carbon atoms or arylalkyl selected from benzyl, phenylethyl and phenylpropyl;
- $R_3$ is hydrogen or lower alkyl of up to 6 carbon atoms;
- $R_4$ is hydrogen or lower alkyl of up to 6 carbon atoms, or when X is oxygen, $R_4$ together with $R_5$ can represent —$CH_2$—O—;
- X is a valency bond, —$CH_2$, oxygen or sulfur;
- Ar is selected from phenyl, naphthyl, indanyl and tetrahydronaphthyl;
- $R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or
- $R_5$ and $R_6$ together represent methylenedioxy;

or a pharmaceutically acceptable salt thereof. These compounds are useful in the treatment of Alzheimer's disease.

Most preferably, the present invention provides a new method for inhibiting the formation of the neurotoxic βA4 oligomeric aggregate using a compound of Formula IV, better known as carvedilol or (1-(carbazol-4-yloxy-3-[[2-(o-methoxyphenoxy)ethyl]amino]-2-propanol):

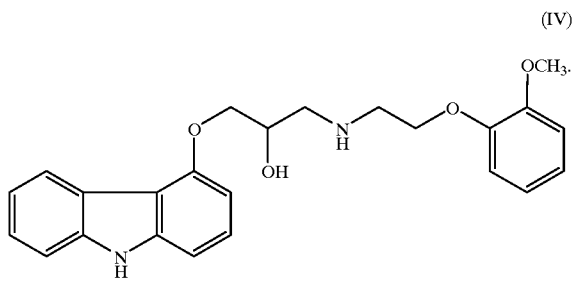

(IV)

This compound is useful in the treatment of Alzheimer's disease.

Since Formula I compounds are amyloidosis inhibitors, these compounds would be useful not only in the treatment of Alzheimer's disease, but they would also be useful in the treatment of chronic inflammation, multiple myelomas, Type II diabetes and Creutzfeldt-Jacob disease. Additionally, the compounds of the instant invention may be useful in treating cardiac problems in old age familial amyloid polyneuropathy, and they may also prevent the need for long-term dialysis.

Formula I compounds, of which carvedilol is exemplary, are novel multiple action drugs useful in the treatment of mild to moderate hypertension. Carvedilol is known to be both a competitive non-selective β-adrenoceptor antagonist and a vasodilator, and is also a calcium channel antagonist at higher concentrations. The vasodilatory actions of carvedilol result primarily from $α_1$-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug in animals, particularly in humans. See Willette, R. N., Sauermelch, C. F. & Ruffolo, R. R., Jr. (1990) *Eur. J. Pharmacol.*, 176, 237–240; Nichols, A. J., Gellai, M. & Ruffolo, R. R., Jr. (1991) *Fundam. Clin. Pharmacol.*, 5, 25–38; Ruffolo, R. R., Jr., Gellai, M., Hieble, J. P., Willette, R. N. & Nichols, A. J. (1990) *Eur. J. Clin. Pharmacol.*, 38, S82–S88; Ruffolo, R. R., Jr., Boyle, D. A., Venuti, R. P. & Lukas, M. A. (1991) *Drugs of Today*, 27, 465–492; and Yue, T.-L., Cheng, H., Lysko, P. G., Mckenna, P. J., Feuerstein, R., Gu, J., Lysko, K. A., Davis, L. L. & Feuerstein, G. (1992) *J. Pharmacol. Exp. Ther.*, 263, 92–98.

The antihypertensive action of carvedilol is mediated primarily by decreasing total peripheral vascular resistance without causing the concomitant reflex changes in heart rate commonly associated with other antihypertensive agents. Willette, R. N., et al. supra; Nichols, A. J., et al. supra; Ruffolo, R. R., Jr., Gellai, M., Hieble, J. P., Willette, R. N. & Nichols, A. J. (1990) *Eur. J. Clin. Pharmacol.*, 38, S82–S88. Carvedilol also markedly reduces infarct size in rat, canine and porcine models of acute myocardial infarction, Ruffolo, R. R., Jr., et al., *Drugs of Today*, supra, possibly as a consequence of its antioxidant action in attenuating oxygen free radical-initiated lipid peroxidation. Yue, T.-L., et al. supra.

According to the instant invention, compounds which are dual non-selective β-adrenoceptor and $α_1$-adrenoceptor antagonists, in particular the compounds of Formula I, preferably carvedilol, treat amyloid diseases. These compounds inhibit the formation of the neurotoxic βA4 oligomeric aggregate, and, therefore, said compounds are useful for treating Alzheimer's disease.

Some of the compounds of Formula I are known to be metabolites of carvedilol. Certain preferred compounds of the present invention, that is, the compounds of Formula I wherein A is the moiety of Formula II wherein R1 is —H, R2 is —H, R3 is —H, R4 is —H, X is O, Ar is phenyl, R5 is ortho —OH, and R6 is —H, and one of $R_7$, $R_9$, or $R_{10}$ is —OH, are metabolites of carvedilol.

Compounds of Formula I may be conveniently prepared as described in U.S. Pat. No. 4,503,067. Reference should be made to said patent for its full disclosure, the entire disclosure of which is incorporated herein by reference.

Pharmaceutical compositions of the compounds of Formula I, including carvedilol, may be administered to patients according to the present invention in any medically acceptable manner, preferably orally. For parenteral administration, the pharmaceutical composition will be in the form of a sterile injectable liquid stored in a suitable container such as an ampoule, or in the form of an aqueous or nonaqueous liquid suspension. The nature and composition of the pharmaceutical carrier, diluent or excipient will, of course, depend on the intended route of administration, for example whether by intravenous or intramuscular injection Pharmaceutical compositions of the compounds of Formula I for use according to the present invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinyl-pyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Dosing in humans for the treatment of disease according to the present invention should not exceed a dosage range of from about 3.125 to about 50 mg of the compounds of Formula I, particularly carvedilol, preferably given twice daily. As one of ordinary skill in the art will readily comprehend, the patient should be started on a low dosage regimen of the desired compound of Formula I, particularly carvedilol, and monitered for well-known symptoms of intolerance, e.g., fainting, to such compound. Once the patient is found to tolerate such compound, the patient should be brought slowly and incrementally up to the maintenance dose. The choice of initial dosage most appropriate for the particular patient is determined by the practitioner using well-known medical principles, including, but not limited to, body weight. In the event that the patient exhibits medically acceptable tolerance of the compound for two weeks, the dosage is doubled at the end of the two weeks and the patient is maintained at the new, higher dosage for two more weeks, and observed for signs of intolerance. This course is continued until the patient is brought to a maintenance dose.

This invention further provides a method for treating Alzheimer's disease which comprises administering stepwise or in physical combination a compound of Formula I and a cognition enhancer, such as Memric. The compound known as Memric is [R-(Z)]-(methoxyimino)-(1-azabicyclo [2.2.2]oct-3-yl)acetonitrile monohydrochloride. The methods for its preparation are disclosed in EP-A-0392803, WO95/31456 and WO93/17018.

The dose of Memric will vary in the usual way with the seriousness of the disorder, the weight of the sufferer, and the relative efficacy of the compound. However, as a general guide suitable daily doses below 0.01 mg/g more particularly 0.003 mg/kg and below, for example 0.0001–0.003 mg/kg, such as 0.00035–0.003 mg/kg, 0.0007–0.003 mg/kg, 0.0001–0.0007 mg/kg or 0.00035–0.002 mg/kg. Suitable unit doses to achieve such daily doses are 5, 12.5, 25, 50 or 75 g, administered twice daily and, in the case of 50 g, once daily.

It will be appreciated that the actual preferred dosages of the compounds being used in the compositions of this invention will vary according to the particular composition formulated, the mode of administration, the particular site of administration and the host being treated.

No unacceptable toxicological effects are expected when the compounds of Formula I are used according to the present invention.

The examples which follow are not intended to limit the scope of this invention, but are provided to illustrate how to use the compounds of this invention. Many other embodiments will be readily apparent to those skilled in the art.

EXPERIMENTAL

Determination of the Inhibition of Beta-Amyloid Peptide Aggregation by Immunoassay Beta-amyloid (1–40) peptide from Bachem UK was dissolved in 0.1% acetic acid at 2 mg/ml and further diluted to 55 ug/ml in phosphate buffered saline (Sigma P4417) containing 0.02% Tween 20 (PBS-Tween). Candidate inhibitors were dissolved in DMSO at 10 mg/ml and further diluted in PBS-Tween. For each candidate inhibitor, 45 ul of 55 ug/ml peptide solution was incubated with 5 ul of appropriately diluted inhibitor overnight at 37° C. in Linbro Titertek EIA II shallow well plates (ICN, EIA II Microplates, cat no. 76-181-04). Plates were sealed during all incubations with Dynatech Labs, cat # 001-010 3501 plate sealers.

For the immunoassay, plates (Gibco BRL, flat bottom 96 well plate, catalogue # 1-67008-A) were coated (overnight at 4° C.) with 2F12 capture antibody, raised to beta-amyloid 1–16 peptide, at 1:3000 in PBS. After coating, antibody solution was aspirated and plates were blocked by incubating for 60 minutes at 37° C. with 1% gelatine v/v (Amersham RPN416), 2.5% goat serum v/v (Sigma G9023) in assay buffer (50 mM Tris HC, 150 mM NaCl, 0.5% bovine gamma globulins, 0.05% Tween 20, pH 7.4, passed through a 0.2 um filter before use). Following blocking, plates were washed 4×250 ul with phosphate buffered saline with Tween 20 (Sigma Cat No P3563). To assay aggregated peptide content of samples incubated with candidate inhibitors, samples were diluted with assay buffer and 50 ul aliquots containing the equivalent of 20 ng beta amyloid 1–40 were added to the wells of the 2F12 coated plate. The detection antibody was a dextran-biotin conjugated 2F12 fab fragment: this antibody was diluted 1:3000 in assay buffer. The 2F12 coated plate containing beta-amyloid 140 and 150 ul of detection antibody was incubated overnight at 4° C. Plates were subsequently washed (4×250 ul) with phosphate buffered saline with Tween 20.

Quantitation of peptide-antibody complexation was achieved by the binding of strepatavidin-Europium. To each well was added 200 ul streptavidin-Europium (Wallac, Catalogue # 1244-360) diluted 1:500 in 0.5% BSA, 0.05% γ Globulin, 0.01% Tween 20, 20 uM DTPA (Sigma D 6518) in Tris buffered saline pH 7.4. Plates were incubated at room temperature for 60 minutes before washing with phosphate buffered saline. Finally, 200 ul of enhancer solution (Wallac, Catalogue # 1244-105) was added to each well and the plate was shaken for 5 minutes at room temperature before measurement of emission by time-resolved fluorescence on a Wallac 1234 Delfia Fluorometer.

Beta amyloid 1–40, which had been aggregated as described above, produced fluorescence readings some 30 to 50 fold greater than background. This increase in fluorescence was prevented when suitable inhibitors were included in the incubation. Peptide which had not been preincubated gave fluorescence readings only 2 to 3 times background. Thus, the increase on incubation is attributable to the detection of aggregated peptide.

Determination of the Inhibition of the Formation of Toxic Aggregates of Beta-Amyloid 1–40 Peptide Beta-amyloid (1–40) peptide from Bachem UK was dissolved in 0.1% acetic acid at 2 mg/ml and further diluted to 55 ug/ml in phosphate buffered saline (Sigma P4417) containing 0.02% Tween 20 (PBS-Tween). Candidate inhibitors were dissolved in DMSO at 10 mg/ml and further diluted in PBS-Tween. For each candidate inhibitor, 45 ul of 55 ug/ml peptide solution was incubated with 5 ul of appropriately diluted inhibitor overnight at 37° C. in Linbro Titertek EIA II shallow well plates (ICN, EIA II Microplates, cat no. 76-181-04). Plates were sealed with Dynatech Labs (cat # 001-010 3501) plate sealers.

MTT (3(4,5-dimethylthiazol-2-yl)-2,5-diphenyl tetrazolium bromide—Sigma) is a metabolic dye taken up by the mitochondria of viable cells and metabolised, yielding a blue formazan crystalline product. This product can by solubilised and the optical density of the blue solution generated is proportional to the mitochondrial activity (viability) of the cells.

For the assessment of toxicity, IMR32 human neuroblastoma cells (ECACC, Porton Down, UK) were plated at $6 \times 10^4$ cells/cm$^2$ in a 96 well microtitre plate (Nunc) in a volume of 100 ul growth medium (DMEM:Hams F12 1:1) per well and incubated for 2 h (CO2 incubator, 37° C.). Incubated beta-amyloid 140 solutions containing candidate inhibitors were diluted in growth medium to produce final (in contact with cells) beta-amyloid 140 concentrations of 0.1 to 10 ng/ml, and added to the IMR32 cells. Vehicles are included in every assay. Plates were incubated overnight (CO2 incubator, 37° C.). To each well was then added 50 ul of MTT solution (5 mg/ml in DMEM:F12/0.4% DMSO) added to each well and plates were incubated for a further 4 hours (CO2 incubator, 37° C.). Medium was then aspirated and formazan product dissolved by addition of 200 ul of DMSO and 25 ul of Sorensen's glycine buffer (0.1M glycine, 0.1M NaCl, pH 10.5 with 0.1M NaOH). Plates were read at 590 nm and inhibition of toxicity assessed as the difference in OD reading between cells in the presence and absence of candidate inhibitors.

RESULTS

1) Immunoassay Results

Beta-amyloid 1–40 (50 ug/ml) was incubated, as described, with carvedilol or analogues. Aggregated peptide content of incubates was determined by immunoassay and inhibition determined as the decrease in the maximally observed fluorescence reading.

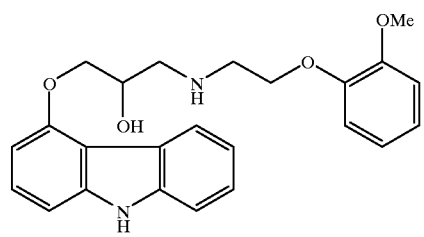

Carvedilol IC$_{50}$ 38 uM (n = 6)

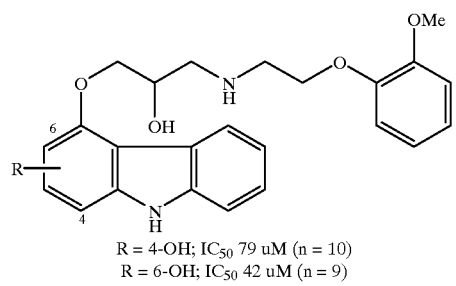

R = 4-OH; IC$_{50}$ 79 uM (n = 10)
R = 6-OH; IC$_{50}$ 42 uM (n = 9)

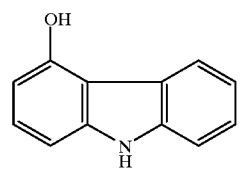

IC$_{50}$ 450 uM (n = 3)

2) Inhibition of Toxic Aggregate Formation in IMR32 Cells

In the example below, 50 ug/ml beta-amyloid 1–40 was incubated overnight with 50 ug/ml carvedilol (or vehicle). The sample was then diluted in growth medium and cells challenged with 0 to 10 ng/ml beta-amyloid 1–40. In the absence of carvedilol, beta-amyloid 1–40 produced a concentration-dependent decrease in MTT reduction over the peptide range tested. The inclusion of carvedilol during the aggregation step resulted in a marked shift to the right in the concentration-response curve, such that no decrease in MTT reduction was observed at 0.1 to 1 ng/ml of peptide.

Results:

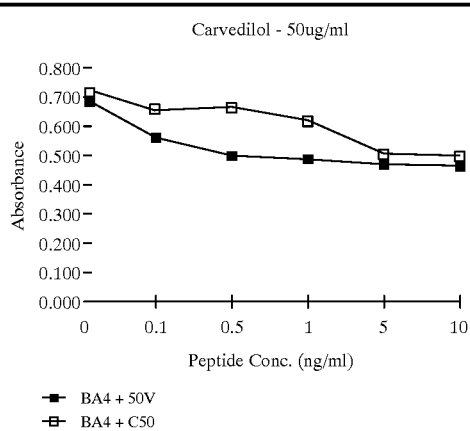

The foregoing are illustrative of the use of the compounds of this invention. This invention, however, is not limited to the precise embodiments described herein, but encompasses all modifications within the scope of the claims which follow.

What is claimed is:

1. A method for treating amyloid diseases which comprises administering to a mammal in need thereof an effective amount of a compound which is a dual non-selective β-adrenoceptor and $α_1$-adrenoceptor antagonist.

2. The method according to claim 1 wherein the compound is a compound of Formula I:

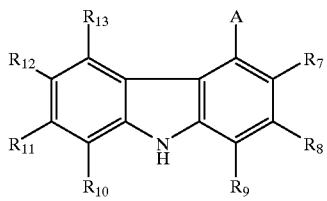

(I)

wherein:

$R_7$–$R_{13}$ are independently —H or —OH; and

A is H, —OH, or a moiety of Formula II:

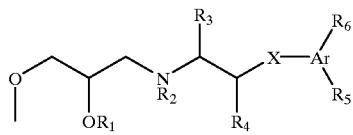

(II)

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —CH$_2$—O—;

X is a valency bond, —CH$_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkylsulphinyl of up to 6 carbon atoms and lower alkylsulphonyl of up to 6 carbon atoms; or $R_5$ and $R_6$ together represent methylenedioxy;

or a pharmaceutically acceptable salt thereof.

3. The method according to claim 1 wherein the compound is a compound of Formula III:

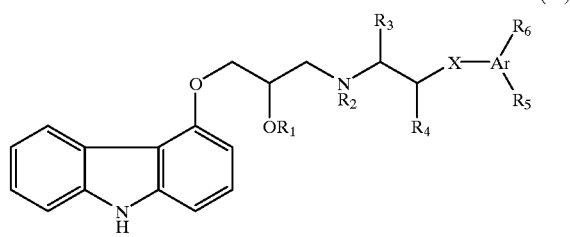

(III)

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —CH$_2$—O—;

X is a valency bond, —CH$_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkylsulphinyl of up to 6 carbon atoms and lower alkylsulphonyl of up to 6 carbon atoms; or or a pharmaceutically acceptable salt thereof.

4. The method according to claim 1 wherein the compound is carvedilol.

5. A method for treating Alzheimer's disease which comprises administering to a mammal in need thereof an effective amount of a compound which is a dual non-selective β-adrenoceptor and $α_1$-adrenoceptor antagonist.

6. The method according to claim 5 wherein the compound is a compound of Formula I:

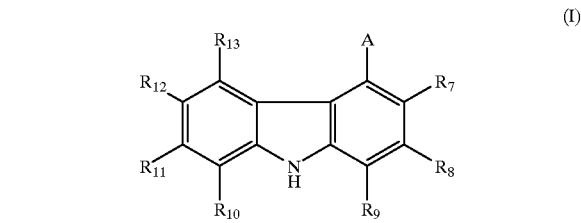

(I)

wherein:

$R_7$–$R_{13}$ are independently —H or —OH; and

A is H, —OH, or a moiety of Formula II:

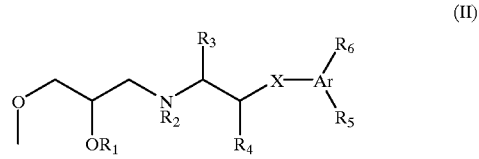

(II)

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

or a pharmaceutically acceptable salt thereof.

7. The method according to claim 5 wherein the compound is a compound of Formula III:

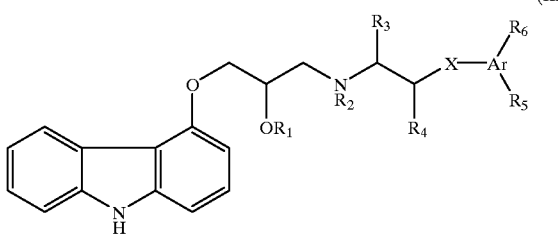

(III)

8. The method according to claim 5 wherein the compound is carvedilol.

9. A method for treating Alzheimer's disease which comprises administering stepwise or in physical combination a compound of Formula I as defined in claim 6 and a cognition enhancer.

10. The method according to claim 9 wherein the compound of Formula I is carvedilol.

11. The method according to claim 9 wherein the cognition enhancer is Memric.

* * * * *